(12) United States Patent
Roseberry et al.

(10) Patent No.: US 7,828,940 B2
(45) Date of Patent: Nov. 9, 2010

(54) ONSITE CHEMISTRY AIR FILTRATION SYSTEM

(76) Inventors: Jeffrey L. Roseberry, 2656 Broadway Ave., Evanston, IL (US) 60201; Robert A. Darling, 1015 Russell Point, Suwanee, GA (US) 30024

( * ) Notice: Subject to any disclaimer, the term of this patent is extended or adjusted under 35 U.S.C. 154(b) by 0 days.

(21) Appl. No.: 12/635,510

(22) Filed: Dec. 10, 2009

(65) Prior Publication Data

US 2010/0086436 A1    Apr. 8, 2010

Related U.S. Application Data

(63) Continuation of application No. 11/465,432, filed on Aug. 17, 2006, now Pat. No. 7,651,555.

(60) Provisional application No. 60/708,951, filed on Aug. 17, 2005.

(51) Int. Cl.
*B01D 39/00* (2006.01)
*B01D 47/00* (2006.01)
*B03C 3/68* (2006.01)
*B03C 3/00* (2006.01)
*A62B 7/08* (2006.01)
*B01J 19/08* (2006.01)

(52) U.S. Cl. ............... 204/157.3; 96/22; 96/18; 96/19; 96/63; 96/223; 422/120; 422/121; 422/122; 422/186.3; 423/210; 95/273

(58) Field of Classification Search ............... 96/22, 96/18, 19, 63, 123; 422/120–122, 186, 186.3; 423/210; 95/273; 204/157.3
See application file for complete search history.

(56) References Cited

U.S. PATENT DOCUMENTS 3,505,989 A    4/1970    Truhan
(Continued)

FOREIGN PATENT DOCUMENTS

WO    2005/089908    9/2005

*Primary Examiner*—Duane Smith
*Assistant Examiner*—Amber Orlando
(74) *Attorney, Agent, or Firm*—Levenfeld Pearlstein, LLC

(57) ABSTRACT

An onsite chemistry air filtration system to remove gaseous contaminants from air is disclosed. The onsite chemistry air filtration system of the present invention comprises: a conventional particulate filtration section, a photochemical filtration section, a static gas phase filtration section and a catalytic filtration section. The conventional particulate filtration section captures solids and condensables. In the photochemical filtration section, UV lamps generate bio-destruction and surface photochemical activity on a semiconductor catalyst material, provide a radiation source to irradiate airborne contaminant molecules and to energize their states to promote reactions and generate airborne ozone and radicals. In the static gas phase filtration section, gas phase filtration media is used to capture contaminants, concentrate them in a relatively confined space and allow airborne generated chemistries to concentrate and react in-situ, thereby creating a regeneration effect on the media. In the catalytic filtration section, catalytic media scavenges and converts airborne radicals and ozone to harmless by-products.

20 Claims, 1 Drawing Sheet

U.S. PATENT DOCUMENTS

| | | |
|---|---|---|
| 4,256,694 A | 3/1981 | McAllister et al. |
| 4,684,380 A | 8/1987 | Leichnitz |
| 4,694,179 A | 9/1987 | Lew et al. |
| 4,963,166 A | 10/1990 | Hoyt et al. |
| 5,086,804 A | 2/1992 | Ngai |
| 5,430,228 A | 7/1995 | Ciambrone et al. |
| 5,564,065 A | 10/1996 | Fleck et al. |
| 5,616,172 A | 4/1997 | Tuckerman et al. |
| 5,935,525 A | 8/1999 | Lincoln et al. |
| 6,315,963 B1 | 11/2001 | Speer |
| 6,491,883 B2 | 12/2002 | Mort et al. |
| 6,500,387 B1 | 12/2002 | Bigelow |
| 6,752,970 B2 | 6/2004 | Schwartz et al. |
| 6,910,445 B1 | 6/2005 | Manthei et al. |
| 7,045,096 B2 | 5/2006 | D'Ottone |
| 7,332,020 B2 | 2/2008 | Tanaka et al. |
| 2002/0139124 A1 | 10/2002 | Palermo |
| 2003/0133832 A1 | 7/2003 | D'Ottone |
| 2007/0193448 A1 | 8/2007 | Tanaka et al. |

ONSITE CHEMISTRY AIR FILTRATION SYSTEM

CROSS-REFERENCE TO RELATED APPLICATIONS

This application is a continuation of U.S. application Ser. No. 11/465,432 filed on Aug. 17, 2006, which claims the benefit of U.S. Provisional Patent Application Ser. No. 60/708,951, filed on Aug. 17, 2005.

BACKGROUND OF THE INVENTION

The present invention relates generally to the field of air filtration and purification and, more particularly, to a complete onsite chemistry air filtration system that enables reactant chemistries to be dynamically generated, contained and controlled onsite for the purpose of removing undesirable contaminants from air. The present invention synthesizes multiple technologies to achieve this end.

Airborne particulate filtration has existed for perhaps hundreds of years with the goal of removing solid particulates from air, typically using a filter comprising a fine web of porous media through which the solid particulates cannot pass, yet gaseous molecules can pass. The size of the pores in the filter media determines the efficiency of the filter (efficiency in this case referring to the maximum sized particulate that may pass through the filter). Such filters sometimes are charged or enhanced with an electrostatic field to increase particulate removal efficiency without reducing media pore size, which would undesirably increase the gas flow pressure drop across the media. Nevertheless, such filters still allow gases to pass through.

Gas phase filtration was introduced in the 1960s to remove gases from the airstream using dry media. In gas phase filtration systems, media is selected to suit the particular contaminant(s) and is usually carbon- or alumina-based. Media may be activated through processing treatments and may be impregnated with additional chemistry to increase capacity and selectiveness of removal.

Most current commercial gas phase filtration applications use either carbon or alumina impregnated with potassium permanganate. Carbon acts by attracting and loosely holding undesirable airborne chemicals. Permanganate impregnated alumina acts as an oxidation media and chemically changes contaminant gases to more stable molecules of their component parts.

However, some chemicals, such as ammonia, require reduction chemistry for removal and, therefore, such chemicals typically have been ignored by prior art filtration systems due to the fact that a completely separate stage of media would be required. Additionally, the capacity for impregnated and activated static media is finite and presents a time-consuming and expensive limitation to the prior art.

In gas phase filtration systems, a certain amount of residence time (the time the gas is exposed to the filtration media) is required, and once the reactive media depth is reduced, residence time also may be reduced below an acceptable figure, resulting in gas bypass and breakthrough. Thus, once the filtration media has been reacted or saturated, the removal efficiency of the filtration system drops significantly. In order to maintain high removal efficiency rates, it is necessary to discard a substantial amount of media, which may be only marginally used. Discarding media that is only partially used unnecessarily increases costs.

Ultraviolet ("UV") light in selective wavelengths has been found to have favorable properties in air filtration. For example, in certain wavelengths it can act destructively on thymine in microorganism DNA, thus preventing replication. Radiation also can be absorbed by molecules "in transit" through an air filtration system, creating energized state where chemical reactions are far more likely to occur. Several paths are possible for a return to a less active state.

Further, in photochemical reactions, UV radiation (generally less than 385 nm) absorbed on the surface of a photocatalytic material generates highly reactive electrons and holes. Photocatalytic adsorbates with suitable redox potentials undergo electron transfer processes at the material surface. For example, UV radiation promotes electrons from the valence band into the conduction band of a titanium dioxide semiconductor photocatalytic material. In an air filtration context, destruction of volatile organic compounds ("VOCs") takes place through reactions with molecular oxygen or through reactions with hydroxyl radicals and super-oxide ions formed after the initial production of highly reactive electron and hole pairs.

Additionally, and quite importantly in the present invention, UV light in the vacuum-ultraviolet ("VUV") range (less than 200 nm) also generates ozone and almost completely breaks down water molecules to H and OH. The latter hydroxyl radical is one of the most powerful oxidizing agents known with an $E°=+2.7$ v in acid solution.

The onsite chemistry air filtration system of the present invention marries and synthesizes a number air technologies to create the unique synergistic effect—a single, complete air filtration system that uses complementary chemical processes to dynamically generate, contain and control reactant chemistries. No air filtration system known in the prior art offers such a complete system.

Accordingly, there exists a need for an improved air filtration system to overcome the limitations found in the prior art and to create a nearly self-sustaining device. Desirably, the air filtration system is configured to advantageously combine a series of air filtration methods and technologies in sequence for filtering a wide array of gaseous contaminants. More desirably, the air filtration methods and technologies in such a system complement one another to dynamically generate, contain and control the reactant chemistries of the air filtration methods and technologies. Most desirably, such a system may be easily installed and retrofit into existing air handling systems.

BRIEF SUMMARY OF THE INVENTION

The onsite chemistry air filtration system of the present invention is a complete system for filtering a wide array of broad-spectrum gaseous contaminants on a dynamic and continuous basis. Additionally, in some embodiments, the system of the present invention has significant biological contaminant reduction capabilities, for reducing airborne bio-matter, such as bacteria, molds and viral matter.

The arrangement and sequence of the filtration and chemical processes of the system, and the dynamic onsite chemistry generation of the system, result in a very high system removal efficiency, and the system maintains straight-line removal efficiency for long periods of time.

Until now, the standard approach to filtering multiple gas phase chemistries from indoor air was to trap them on carbon, react them with a chemical on carbon or activated alumina, or to use a liquid system with chemicals and pass the air through the liquid phase to react with the gas phase. These approaches all suffer from the inherent limitations of the chemistries initially installed in the systems. To keep such systems working at peak capability the media or chemical needs to be replaced, and replaced frequently if the contaminant loading is high. This is expensive both in terms of media costs and labor, and time to do the replacing. Moreover, the activity levels of impregnated media are also lower than dynamically generated chemistry.

In the preferred embodiment, the onsite chemistry air filtration system of the present invention comprises the following general components: a conventional particulate filtration section, a photochemical filtration section, a static gas phase filtration section and a catalytic filtration section.

The conventional particulate filtration section captures solids and condensables. The present invention incorporates the ability to remove all airborne particles with a sequence of filters up to MERV ("Minimum Efficiency Reporting Value") 14 efficiency that protects the downstream chemistry sections of the invention.

In the photochemical filtration section, UV lamps generate bio-destruction and surface photochemical activity on a photocatalytic material. In the preferred embodiment, the photocatalytic material is a semiconductor catalyst. The surface chemistry of the semiconductor catalyst is dynamic and provides oxidation and reduction chemistry. In some embodiments of the present invention, the semiconductor catalyst surface also may be charged electrostatically to enhance capture rate of large molecules and bio-matter.

The photochemical filtration section also includes UV lamps that provide a radiation source to irradiate airborne molecules passing through the section and to energize their states to promote reactions. Finally, the photochemical filtration section includes additional UV lamps and/or other ozone and radical generation devices (such as corona discharge) that are used to generate airborne chemistry, including ozone, hydroxyl radicals, hydroperoxides, peroxides, super-oxides and others. Such ozone and radical generation devices may or may not be in the airstream.

In one embodiment of the present invention, the photochemical filtration section also may contain electrostatic plates configured to capture particulate matter. The plates contain such matter and allow the matter to be irradiated by the UV lamps for an almost infinite residence time. Such an embodiment typically is used in applications and environments in which bio-matter, such as bacteria, molds, spores, viral and miscellaneous loose bio-matter must be captured and destroyed. Destruction of such matter is more complete in situ rather than in transit because the relatively short radiation exposure time in transit generally is insufficient to adequately break down such matter.

In the static gas phase filtration section, filtration media is used to capture contaminants, concentrate them in a relatively confined space and allow airborne generated chemistries to concentrate and react in-situ. This media is stable and represents a reaction zone where chemicals can be broken down, without transit time constraints, to harmless by-products. This media also is capable of on-site regeneration in situations where airborne chemistry supply exceeds contaminant demand. The static gas phase filtration section may include first stage and second stage filtration sections, if necessary, the second phase filtration section configured to capture any by-products of the upstream reactions (the composition of such beds being dependent on particular gases to be treated).

In the catalytic filtration section, media that has catalytic properties on airborne chemistry scavenges and converts airborne radicals and ozone to harmless by-products such as water vapor and oxygen. The catalytic filtration section additionally may include particulate filtration to capture any initial dust from the various media beds.

Sensors are provided in the preferred embodiment of the onsite chemistry air filtration system of the present invention to enable monitoring of various operating parameters. These sensors provide safety for supply side air and allow the dynamic chemistry production to be managed to meet demand. For example, an ozone sensor allows downstream ozone concentration to be measured in real time. Also, a humidity sensor and control may also be included to maintain proper levels of water in the air depending on the particular system operational environment, and to prevent the dynamic chemistry generation from being operated in undesirable conditions. The system may further include a device to monitor, in real time, the condition of the air entering and/or leaving the system as well as the overall operation and efficiency of the system.

Additionally, various safety devices, such as temperature monitors in the media beds of the static gas phase filtration section may be included. In the preferred embodiment, a temperature monitor in the media bed of the first stage filtration section of the static gas phase filtration allows the temperature of the media bed to be monitored and prevented from reaching unsafe levels. However, other embodiments of the present invention may optionally include monitors in any of the media beds in the static gas phase filtration section.

The onsite chemistry air filtration system of the present invention may include a fan if it is installed as a freestanding unit outside of an air handling system. However, a fan may be unnecessary when the air filtration system of the present invention is integrated with other air handling equipment, as typically may be found in most commercial applications.

Different embodiments of the onsite chemistry air filtration system of the present invention may include different combinations of the preceding components as necessary for a particular application or environment. It will be understood that the present disclosure encompasses all such combinations and embodiments.

A key to the present invention is the process of photochemistry, which is used to generate reactive chemicals for remediation of the contaminants in-situ in the air, on the surface of the semiconductor catalyst and in the subsequent static gas phase stages that follow the photochemical filtration section. Using UV light in the photochemical filtration section with a selected spectrum from 85-300 nm creates several advantageous results.

First, various reactive radicals are created to destroy airborne contaminants on contact. Second, various chemistries are created that travel from the photochemical filtration section to the subsequent static gas phase filtration section and react with contaminants trapped in the media bed(s) of the static gas phase filtration section to enhance the efficiency of the static gas phase filtration section by creating a regenerative effect on the media bed(s). Third, the semiconductor catalyst is activated, creating electrons and holes on the surface of the catalyst that are capable of both reducing and oxidizing chemicals that come in contact with the catalyst. And, fourth, photons are generated that are absorbed by a species. Absorption of photons causes electrons to transfer to outer valance bands, gain activity and, often, behave as different species. This process extends the active life of the media in the static gas phase filtration section.

Marrying gas phase filtration with photochemical filtration eliminates the disadvantage of using photochemical filtration only, as has been done in the prior art, which can generate noxious and harmful by-products that are partial reductions or oxidations of complex molecules. Only by trapping and continuing the destruction of such molecules can the airstream be fully remediated.

The onsite chemistry air filtration system of the present invention is fully scalable and can be used in myriad applications, include residential and low rise buildings, commercial offices and places of business (including high rise buildings), casinos (primarily to address Environmental Tobacco Smoke ("ETS")), ships (for bio, chemical and odor control), military (for chemical and biological control, including mobile, portable or fixed equipment), secure buildings (for total contaminant control), airports, mass transit vehicles (such as buses, railcars and airplanes), automobiles and mining (and other mobile equipment housing personnel).

The onsite chemistry air filtration system of the present invention creates an air purification device that has many times the stoichiometric capacity for gaseous contaminant removal of media-only systems, on-site regeneration of media in the static gas phase filtration section, higher removal efficiency, oxidation and reduction chemistry and benign by-products. It is also possible to provide gaseous filtration "on demand."

Benefits of the onsite chemistry air filtration system of the present invention include reduced energy consumption for buildings, cleaner air, lower filtration system and building operating costs, greatly reduced media consumption, broader spectrum chemical removal capacity, easier installation with side stream air scrubbers, ease of retrofitting existing installations and easily "managed" air cleaning and ventilation.

These and other features and advantages of the present invention will be apparent from the following drawings and detailed description in conjunction with the appended claims.

BRIEF DESCRIPTION OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE PREFERRED EMBODIMENT

Figure 1:
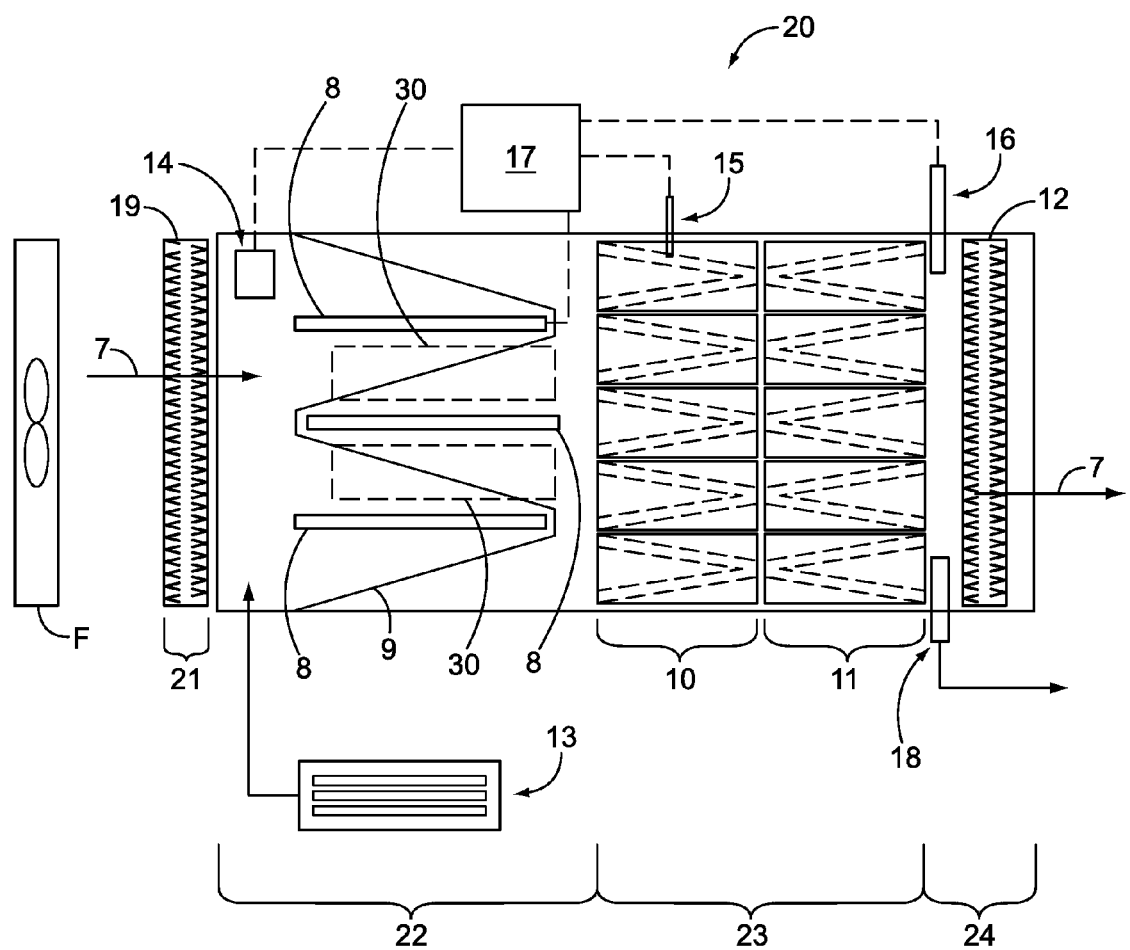
FIG. 1 is a side elevation of the major components of the onsite chemistry air filtration system in the preferred embodiment of the present invention.

While the present invention is susceptible of embodiment in various forms, there is shown in the drawings and will hereinafter be described several preferred embodiments with the understanding that the present disclosure is to be considered an exemplification of the invention and is not intended to limit the invention to the specific embodiments illustrated.

It should be further understood that the title of this section of this specification, namely, "Detailed Description Of The Invention," relates to a requirement of the United States Patent Office, and does not imply, nor should be inferred to limit the subject matter disclosed herein.

The onsite chemistry air filtration system of the present invention is a complete system for removal of gaseous, particulate and biological contaminants, and utilizes multiple technologies that compliment and support each other. The present invention combines and synthesizes several air filtration technologies and, as a system, performs much better than any of the utilized technologies on their own or in other combinations found in the prior art.

As shown in FIG. 1, in the preferred embodiment the onsite chemistry air filtration system 20 is comprised of four primary sections: a conventional particulate filtration section 21, a photochemical filtration section 22, a static gas phase filtration section 23 and a catalytic filtration section 24. The direction of airflow 7 through the preceding components is show in FIG. 1.

As noted above, it should be understood that not every embodiment of the present invention may include each of the four preceding sections and that some sections, such as the catalytic filtration section, for example, may be omitted if not necessary for a particular application.

The onsite chemistry air filtration system 20 of the present invention is, in the preferred embodiment, constructed within an airtight housing that contains the above-identified components. The housing may be constructed of mild steel, galvanized steel, aluminized steel, aluminum, stainless steel or any suitable housing material to support the sections. The housing includes an inlet and outlet to match the system into which it is being integrated, along with the appropriate transitions to the ductwork. Such construction is well known in the prior art. Additionally, when system 20 of the present invention is installed within an HVAC system the housing should be insulated to preserve the temperature of the airstream.

If the onsite chemistry air filtration system is freestanding, as opposed to being installed in an existing air handling system, it will be configured with outlet and inlet grilles, along with access doors and/or panels to permit access to all areas of the system for servicing—from both sides, preferably. In the preferred embodiment of such a system, a window should be included in the photochemical filtration section to permit observation of the UV lamps; however, such a window should be configured to prevent the escape of the UV radiation.

Conventional particulate filtration section 21 is configured to capture airborne solids and condensables. In the preferred embodiment, conventional particulate filtration section 21 comprises a sequence of particle filters 19. Filters 19 are of the type well known in the prior art. In the preferred embodiment, filters 19 are configured to remove all airborne particles up to MERV ("Minimum Efficiency Reporting Value") 14 efficiency.

Filters 19 are configured to protect the UV lamps and catalytic surfaces in photochemical filtration section 22 from dust accumulation. Moreover, since many filtration environments require both particulate and gas phase filtration, filters 19 act as an initial means of particulate filtration. An example of such an environment is cigarette smoke (environmental tobacco smoke, or "ETS"). An ETS cloud is essentially particulates with a gaseous smell. Filters 19 of conventional particulate filtration section 21 remove such particulates.

In the preferred embodiment of the onsite chemistry air filtration system 20 of the present invention, filters 19 include three discrete filters, in sequence, starting with a MERV 8, then a MERV 11, and finally a MERV 14. Importantly, the sequence of filters 19 in conventional particulate filtration section 21 must always be from lowest efficiency to highest efficient in the direction of airflow 7. Each filter in the preferred embodiment is 4 inches deep, however, the present invention is not limited to any particular filter depth, and many prior art filters of appropriate efficiency may be used. Additionally, depending upon the particular application and environment, bag filters and/or HEPA filters may be used to replace or supplement filters 19.

Photochemical filtration section 22 consists of arrays of UV lamps 8. UV lamps 8 serve three primary purposes. First, UV lamps 8 provide a radiation source to irradiate and sterilize airborne molecules passing through photochemical filtration section 22 and to energize their states to promote reactions. Second, UV lamps direct radiation to the surface of a photocatalytic material (semiconductor catalyst 9 in the preferred embodiment), thereby generating bio-destruction and surface photochemical activity on semiconductor catalyst 9. Since the surface chemistry of semiconductor catalyst 9 is dynamic, both oxidation and reduction chemistry are created when semiconductor catalyst 9 is exposed to UV radiation from UV lamps 8. Third, UV lamps 8 generate ozone and radicals used to facilitate additional downstream contaminant-destructing reactions.

UV lamps 8 are electrically powered lamps that generate ultraviolet light in a preferred frequency range. Such lamps are well known in the prior art and are readily commercially available from many sources. In the preferred embodiment, UV lamps 8 are mercury vapor lamps, however, any type of UV lamps that generate the appropriate frequencies may be used.

UV lamps 8 are configured to generate light in the range of 85-300 nm, and more preferably in the range of 150-300 nm. In the preferred embodiment, UV lamps 8 produce light at 185 nm (VUV), as well as light at 254 nm. This is accomplished by using mercury vapor bulbs, which have natural energy peaks at 185 nm and 254 nm. Preferably, UV lamps 8 comprise a combination of mercury vapor bulbs, some of which are filtered to emit UV light only at 254 nm, and some of which are unfiltered and emit light at both 185 nm and 254 nm. It will be understood, however, that any type or combination of bulbs may be used for UV lamps 8 as long as such bulbs emit UV radiation within the preferred frequency range. It will be further appreciated that the particular frequencies of UV lamps 8 may vary without departing from the scope of the present invention, the particular frequencies selected to fit the particular application and/or environment in which system 20 operates, as long as they achieve the desired excitation of the semiconductor catalyst 9 surface to produce highly reactive electron and hole pairs.

The combination of UV light at 185 nm and 254 nm provides several key advantages in the present invention. First, VUV light at 185 nm, the use of which is unknown in the prior art in air filtration systems, promotes ozone and radical generation used to facilitate downstream contaminant-destructing reactions.

Second, UV light at 254 nm excites and raises the potential on the surface of semiconductor catalyst 9, sterilizes airborne molecules by destroying undesirable biological compounds, excites and raises the potential on the surface of airborne molecules to encourage additional reactions and generates photochemical reactions on the surface of semiconductor catalyst 9.

Additionally, it should be noted that while VUV light (100-200 nm) is used in the present invention to generate ozone and radicals, the transmission strength of such light is inherently limited. Bulbs producing such VUV light typically cannot transmit such light far beyond the bulb. Thus, such VUV light generally has no effect on the activation of the surface of semiconductor catalyst 9.

UV lamps 8 can be oriented parallel (as in the preferred embodiment) or transverse to the airflow 7, or anything in between. However, as further discussed below, UV lamps 8 should be oriented to produce the maximum transfer of light energy to semiconductor catalyst 9 in order to generate the most efficient and effective photochemical activity on semiconductor catalyst 9.

As discussed above, photochemical filtration section 22 further comprises a photocatalytic material, semiconductor catalyst 9 in the preferred embodiment. While this disclosure refers to such photocatalytic material as a "semiconductor catalyst," it will be appreciated that the photocatalytic material may be any material with suitable photocatalytic properties, not just a semiconductor. All such materials, as known to those skilled in the art, are included with the scope of the present invention.

Semiconductor catalyst 9 should be a material that responds to UV light such that free radicals and holes are formed in semiconductor catalyst 9. In the preferred embodiment, semiconductor catalyst 9 is titanium dioxide ($TiO_2$). However, those skilled in the art will recognize that other catalytic materials may be used, and the present invention is not limited to the preferred titanium dioxide. Any catalytic material that generates the appropriate surface chemistry may be used.

When such electrons and holes are on the surface of semiconductor catalyst 9, they are highly reactive and break down most absorbates using photocatalyst reactions that include both oxidation and reduction chemistry ("redox"). The surface of semiconductor catalyst 9 is so reactive that semiconductor catalyst 9 acts as a filter. In the event that a material, such as tar (from cigarette smoke), condenses and adheres to the surface of semiconductor catalyst 9, it is systematically dismantled and destroyed by the photocatalytic reactions.

In the preferred embodiment the titanium dioxide semiconductor catalyst 9 is coated onto a substrate. The substrate must be of appropriate strength and rigidity to support the titanium dioxide (in the preferred embodiment) or any other desired semiconductor catalyst material. The substrate also must be chosen to expose the highest surface area of semiconductor catalyst 9 to the radiation of UV lamps 8 without excessively restricting airflow. Many arrangements are possible, but, in the preferred embodiment, the substrate comprises a tubular perforated steel disposed perpendicular to the airflow 7.

In some embodiments of the present invention, the surface of semiconductor catalyst 9 may be charged electrostatically, using techniques known to those skilled in the art, to enhance the adherence and capture rate of large molecules and, particularly, bio-matter.

In some embodiments of the present invention, photochemical filtration section 22 may include an external ozone and radical generation device 13 used to generate airborne chemistry, including ozone, hydroxyl radicals, hydroperoxides, peroxides, super-oxides, and others, if necessary for a particular application or environment. Such an external ozone and radical generation device may include, for example, additional UV lamps and/or a corona discharge. Ozone and radical generation device 13 may or may not be in the airstream.

Ozone and radicals may need to be generated outside of filtration system 20 due to any number of reasons. For example, some applications require ozone and radical generation device 13 to be located remotely and the output ducted in to photochemical filtration section 22 due to space, or other environmental constraints. A high-powered external ozone and radical generation device 13 can generate higher concentrations of ozone and radicals.

Additionally, in some embodiments of the present invention, including the preferred embodiment, photochemical filtration section 22 includes humidity monitor 14. In some applications and environments, humidity needs to be monitored and adjusted. This provides added effectiveness and safety, and, in extreme cases, humidity monitor 14 can be used to activate additional humidity input, such as through external ozone and radical generation device 13 or through other known means. Humidity (water vapor) encourages the chemical reactions that occur in system 20 of the present invention by providing more raw materials to produce hydroxyl, hydroperoxy, peroxides and other radicals.

Moreover, in one embodiment of the present invention, semiconductor catalyst 9 may be replaced, or supplemented by, electrostatically charged plates 30 configured to capture particulate matter. Plates 30 contain such matter and allow the matter to be irradiated by UV lamps 8 for an almost infinite residence time. Such an embodiment typically is used in applications and environments in which bio-matter, such as bacteria, molds, spores, viral and miscellaneous loose bio-matter must be captured and destroyed. Destruction of such matter is more complete in situ rather than in transit because of the increased amount of UV radiation required to destroy the matter.

The preferred embodiment of the onsite chemistry air filtration system of the present invention further includes a static gas phase filtration section 23, having a first stage 10 and an optional second stage 11 filtration section. The preferred embodiment of the present invention includes both first stage filtration section 10 and second stage filtration section 11. First stage filtration section 10 and second stage filtration section 11 each comprise a media bed.

First stage filtration section 10 is configured to capture contaminants in the normal adsorption and absorption process and concentrate them in the pores of the media bed. The media bed in first stage filtration section 10 treats all molecules as contaminants, and, since most of the generated chemistry in photochemical filtration section 22 is oxidative in nature, the media bed reacts with the captured contaminants to destroy them.

The media bed in first stage filtration section 10 provides a surface or shallow depth concentration zone where contaminants are held and bombarded with reactive airborne chemistry from photochemical filtration section 22 until the contaminants are broken down and destroyed. Without being bound to any particular theory, it is believed that because such contaminant destruction occurs before the contaminants are absorbed deeply into the media bed, the media bed of first stage filtration section 10 (at least the portion of the media bed of first stage filtration section 10 closest to photochemical filtration section 22) essentially acts to regenerate itself, thereby greatly extending the life of such media and maintaining the highest efficiency through a continuously cleansed surface.

Additionally, in the event that the contaminant uptake load exceeds the capacity of the dynamic chemistry generated by photochemical filtration section 22, the media bed in first stage filtration section 10 also collects and stores excess gases. Conversely, when the contaminant load is lower than the dynamic chemistry generation rate, the stored contaminants are dismantled and destroyed. Since a contaminant load typically has peaks and valleys, the configuration and interaction of photochemical filtration section 22 and first stage filtration section 10 allows a balance to be achieved with longer media life, less media and lower costs.

The media bed in first stage filtration section 10 preferably is comprised of carbon or alumina-based materials as are well known by those skilled in the art for such purposes, and may or may not be impregnated with alternate chemistries during manufacture to enhance sorption. In the preferred embodiment, a high surface area sorptive material is used for the media bed in first stage filtration section 10, namely activated carbon. As is known in the art, activated carbon has an affinity for attracting and holding chemicals.

In the preferred embodiment, the media bed in first stage filtration section 10 should be about 2 inches deep, or more if possible, but is not restricted to any depth. A deeper media bed is preferred, but if the media bed is too deep (over 6 inches, for example) the pressure drop across the media bed will restrict airflow and increase power requirements. Many arrangements are possible for the media beds in first stage filtration section 10. However, in the preferred embodiment, 24 inch by 24 inch by 2 inch trays of perforated steel or plastic are used to hold the activated carbon media in a pleated fashion such that six or more trays are within a 2 foot by 2 foot face area.

In the preferred embodiment, a first stage media bed temperature monitor 15 is disposed in the media bed of first stage filtration section 10. First stage media bed temperature monitor 15 is a thermocouple in the preferred embodiment. Since contaminant removal typically occurs by oxidation, an exothermic reaction, it is important to monitor the temperature of the media bed. In the unlikely event that heat build up becomes excessive, the thermocouple allows the onsite chemistry air filtration system 20 to be shut down.

In the preferred embodiment, first stage media bed temperature monitor 15 is interactively coupled to a main control unit 17 (discussed below) to shut off UV lamps 8 if the media bed temperature exceeds a predetermined limit. Many temperature limits may be used, but the temperature limit should be well below the flash point of the media bed material. Preferably, an annunciator light is visible on main control unit 17 in the preferred embodiment, indicating that first stage media bed temperature monitor 15 is working and displaying the media bed temperature.

Additionally, in the preferred embodiment, the media beds in first stage filtration section 10 are configured to provide at least 0.1 seconds of air residence time and ideally 0.3 seconds, or more. However, the residence time will vary depending upon application and the operating environment. The higher the load, the longer the necessary residence time.

As discussed above, static gas phase filtration section 23 includes second stage filtration section 11 in the preferred embodiment. Second stage filtration section 11 is configured to capture any by-products of the upstream reactions (from photochemical filtration section 22 and first stage filtration section 10), to act as a safety and to provide additional surge capacity for heavy contaminant loads. It should be understood, however, that second stage filtration section 11 may not be necessary for all applications and environments.

In the preferred embodiment, second stage filtration section 11 includes media beds configured in an identical manner as is in first stage filtration section 10. However, the media used in the media beds in second stage filtration section 11 is different from that in first stage filtration section 10.

In the preferred embodiment, the media used in the media beds of second stage filtration section 11 comprises activated alumina impregnated with potassium permanganate ($KMnO_4$) rather than activated carbon. Activated alumina impregnated with potassium permanganate is well known in the prior art as a gas phase filtration media.

The media in second stage filtration section 11 also may comprise a blend of carbon and alumina impregnated in a fifty-fifty ratio by volume, in one embodiment. However, as recognized by those skilled in the art, myriad other media compositions, blend ratios and impregnates also may be used if dictated by the specific application and/or environmental conditions.

In addition to filtering the by-products of the upstream reactions, second stage filtration section 11 also serves as an indicator bed. When the activated alumina impregnated with potassium permanganate starts to be consumed, it serves as an indication of air bypass from the active carbon media in media bed of first stage filtration section 10. The remaining life of the media bed in second stage filtration section 11 can be determined by analyzing a sample of the media, or, or in the case of activated alumina impregnated with potassium permanganate, monitoring the visual change in color of the media from purple to brown. Other impregnates may be colorless or display a different color.

Additionally, a second stage media bed temperature monitor (not shown) may be included in some embodiments of the present invention if the operating conditions or environment warrant the monitoring of the media bed of second stage filtration section 11.

The onsite chemistry air filtration system 20 in the preferred embodiment of the present invention further includes a catalytic filtration section 24. In catalytic filtration section 24, media that has catalytic properties on airborne chemistry scavenges and converts airborne radicals and ozone to harmless by-products, such as water vapor and oxygen. Catalytic filtration section 24 also may additionally include particulate filtration to capture any initial dust from the media beds in first stage filtration section 10 and section stage filtration section 11 of static gas phase filtration section 23.

In the preferred embodiment, catalytic filtration section 24 comprises a non-woven fiber filter 12 containing a manganese dioxide catalyst trapped in the fiber. In other embodiments, the manganese dioxide may be replaced or combined with carbon. Filter 12 is pleated in the preferred embodiment and is at least 4 inches deep. Filter 12 is configured to stop any dust from the upstream media beds from flowing downstream in the filtered air and to provide a final safety mechanism to prevent radicals generated in photochemical filtration section 22 from traveling beyond system 20. Filter 12 further operates to convert surplus ozone and radicals to oxygen and water.

In the preferred embodiment of the onsite chemistry air filtration system 20 of the present invention, several sensors are disposed throughout the system to monitor various operational variables. For example, as discussed above, humidity monitor 14 preferably is included in photochemical filtration section 22 in order ensure the proper level of humidity is maintained to maximize the level of chemical reactions that occur. Similarly, first stage media bed temperature monitor 15 preferably is disposed in the media bed of first stage filtration section 10 to monitor the heat generated by the exothermic reactions that occur there.

Another sensor included in the preferred embodiment of the onsite chemistry air filtration system 20 of the present invention is an ozone sensor 16. Ozone sensor 16 is of the type well known to those skilled in the art and is configured to monitor the level of ozone being generated by system 20. As is well known, ozone is a harmful gas, and its levels are strictly regulated.

In the preferred embodiment, ozone sensor 16 is disposed in airstream between final stage filtration section of static gas phase filtration section 23 and catalytic filtration section 24. Ozone sensor 16 preferably is positioned to continuously monitor ozone levels and to confirm that exiting ozone levels are below appropriate regulatory levels. Since ozone and highly active chemistry on a dynamic basis are generated upstream, ozone sensor 16 allows system 20 to generate, contain, and manage the various system processes while avoiding a hazardous condition. In the preferred embodiment, ozone sensor 16 is set to shut down UV lamps 8 and/or other device(s) with ozone generating capacity (such as external ozone and radical generation device 13) once a pre-determined ozone level is reached.

In addition to ozone sensor 16, air monitor 18 also is installed in the preferred embodiment. Like ozone sensor 16, air monitor 18 preferably is installed between the final stage filtration section of static gas phase filtration section 23 and catalytic filtration section 24. Air monitor 18 monitors the overall condition of the filtered air exiting system 20 in real time.

Air monitor 18 preferably includes a group of sensors to monitor various operating parameters of system 20. The key operating parameter is total volatile organic compounds (TVOCs) present in the filtered air. TVOCs are the key chemical performance indicator in applications where environmental tobacco smoke ("ETS") or other similar contaminants are being controlled. Also monitored by air monitor 18 may be air temperature, humidity, carbon dioxide concentration and/or carbon monoxide concentration. The output signal of air monitor 18 preferably should be available for local or remote monitoring either at device itself, and/or through a networking protocol such as LON Works or BACNET. Ideally, the data from air monitor 18 should be retrievable externally such as via the Internet, wirelessly or through a building management system. As sensor technology advances, other sensors may be implemented in air monitor 18 to monitor additional operational parameters of system 20.

As shown in FIG. 1, the onsite chemistry air filtration system 20 in the preferred embodiment of the present invention also includes a main control unit 17. Control unit 17 is interactively coupled with humidity monitor 14, UV lamps 8 in photochemical filtration section 22, first stage media bed temperature monitor 15 and ozone sensor 16. Control unit 17 is configured to monitor the data received from humidity monitor 14, first stage media bed temperature monitor 15 and ozone sensor 16 and to adjust the operating parameters of the system (such as increasing humidity or disabling UV lamps 8) as necessary to ensure that system 20 operates safely and efficiently.

The onsite chemistry air filtration system 20 of the present invention also may include a fan (F) if it is installed as a freestanding unit outside of an existing air handling system. However, fan (F) is unnecessary when system 20 of the present invention is integrated with air handling equipment, as typically may be found in most commercial applications. When present, fan (F) may be disposed before, within or after system 20. By way of example, as shown in FIG. 1, fan (F) is disposed before the entrance of system 20 in order to force air into system 20 in the direction of airflow 7. In any event, in the preferred embodiment, the total airflow volume should not exceed 2,000 cubic feet per minute per 2 foot by 2 foot square face area, or 500 feet per minute velocity; however, slower airflow volume is preferred.

Removing chemical contaminants by chemical reaction takes place at several sites in the preferred embodiment of the onsite chemistry air filtration system 20 of the present invention, including: airborne reactions due to UV radiation on contaminant molecules in photochemical filtration section 22; surface activity from photochemistry and semiconductor catalization in photochemical filtration section 22; airborne and media bed reaction from ozone and radicals in static gas phase filtration section 23; oxidation from permanganate and neutralization catalysis of excess ozone and radicals in static gas phase filtration section 23 and catalytic filtration section 24.

A sample selection of the various reactions that occur in the onsite chemistry air filtration system 20 of the present invention follows. The examples are merely illustrative and represent a start point and a final result—there are invariably intermediate states and reactions. The reactions are dynamic and as molecules increase in size and complexity, the dismantling process becomes more involved.

Several reactions can take place as an atom or molecule is elevated to an excited state when exposed to radiation, hv. These include:

Ionization. Occurs typically at lower wavelengths.

$$NO + hv \rightarrow NO(+) + e$$

$$O_2 + hv \rightarrow O_2(+) + e$$

Intermolecular Reaction. Radiation can establish the right conditions for a complex reaction. Photosynthesis is described below.

$$nCO_2 + nH_2O + hv \rightarrow (CH_2O)n + nO_2$$

Dissociation. Molecules are split.

$$H_2O + hv \rightarrow H + OH$$

$$H_2O_2 + hv \rightarrow 2\ OH$$

$$H_2S + hv \rightarrow H + SH$$

$$NH_3 + hv \rightarrow NH_2 + H$$

$$O_2 + hv \rightarrow O + O$$

$$O_3 + hv \rightarrow O + O_2$$

$$SO_2 + hv \rightarrow SO + O$$

$$SO_3 + hv \rightarrow SO + O_2$$

$$\text{Aldehyde ``R''}CHO + hv \rightarrow RH + CO$$

Direct Reaction. Reactive species combine.

$$O + O \rightarrow O_2$$

Photocatylist/Semiconductor. Surface chemistry is generated by the action of radiation on the surface of semiconductor catalyst 9. Electrons $e^-$ and holes $h(+)$ are formed (1). If an oxygen molecule is in contact with an electron $e^-$ before it re-combines, a superoxide ion is formed (2). A water molecule will react with the opposite positively charged hole to form hydroxyl radical (3). The negatively charged superoxide will also react with a positive hole to form hydroperoxy (4), which continues to form peroxide (5), which under radiation breaks down to form more hydroxyl radicals (6).

$$\text{Semiconductor ``A''} + hv \rightarrow e^- + h(+) \tag{1}$$

$$O_2 + e^- \rightarrow O_2^- \text{ (superoxide)} \tag{2}$$

$$h(+) + H_2O \rightarrow .OH + h(+) \text{ (hydroxyl radical)} \tag{3}$$

$$O_2^- + h(+) \rightarrow HO_2 \text{. (hydroperoxy)} \tag{4}$$

$$HO_2 . + e^- + h(+) \rightarrow H_2O_2 \text{ (peroxide)} \tag{5}$$

$$H_2O_2 + hv \rightarrow 2.OH \tag{6}$$

Most contaminants that adhere to the surface of semiconductor catalyst 9 also will be broken down, including biological molecules.

The hydroxyl radical is a key component and is one of the most powerful oxidizing agents known with an electron potential of +2.7 v. This is much stronger than chlorine, ozone and peroxide. It is also formed by the breakdown of ozone in the presence of water vapor.

Hydroxyl Reactions. These highly active reactions take place at close to diffusion-controlled rates. This is extremely significant when dealing with organic compounds. The hydroxyl radical can systematically dismantle molecules. It can behave in many ways and three examples are given below (respectively) of extracting a hydrogen to allow a lower energy state in water; joining a compound by breaking a double bond and what can happen when two radicals collide.

$$CH_3OH + .OH \rightarrow .CH_2OH + H_2O \text{ (Methanol)}$$

$$CHCl = CCl_2 + .OH \rightarrow .CHCl - C(OH)Cl_2 \text{ (tri-chlorethylene)}$$

$$HO_2 . + .OH \rightarrow O_2 + H_2O \text{ (hydroperoxy)}$$

Ozone Reactions. "Simplified" and intermediate steps such as superoxides, peroxides, hydroxyls and hydroperoxies are clearly implicated. Ozone is formed by the action of UV at short enough wavelengths to break the oxygen bonds and the highly reactive sub species combine with other atoms and molecules, some of which forms ozone, $O_3$. It is naturally unstable. Most of this reaction will take place inside the media bed of first phase filtration section 10 of static gas phase filtration section 23 where contaminants are concentrated and bombarded with chemistry.

$$C_2H_4O_2 + 4\ O_3 \rightarrow 2\ CO_2 + 2\ H_2O + 4\ O_2 \text{ (acetic acid)}$$

$$C_3H_6O + 8\ O_3 \rightarrow 3\ CO_2 + 3\ H_2O + 8\ O_2 \text{ (acetone)}$$

$$HCHO + 2\ O_3 \rightarrow CO_2 + H_2O + 2\ O_2 \text{ (formaldehyde)}$$

$$CH_3CHOHCH_3 + 9\ O_3 \rightarrow 3\ CO_2 + 4\ H_2O + 9\ O_2 \text{ (isopropyl alcohol)}$$

$$CH_3COC_2H_5 + 11\ O_3 \rightarrow 4\ CO_2 + 4\ H_2O + 11\ O_2 \text{ (methyl ethyl ketone)}$$

$$C_6H_6 + 11\ O_3 \rightarrow 6\ CO_2 + 3\ H_2O + 11\ O_2 \text{ (benzene)}$$

$$C_4H_{10} + 13\ O_3 \rightarrow 4\ CO_2 + 5\ H_2O + 13\ O_2 \text{ (butane)}$$

$$2\ CH_3CCl_3 + 14\ O_3 \rightarrow 4\ CO_2 + 3\ H_2O + 3\ Cl_2O + 14\ O_2 \text{ (methyl chloroform)}$$

$$2\ HCN + 5\ O_3 \rightarrow 2\ CO_2 + H_2O + N_2 + 5\ O_2 \text{ (hydrogen cyanide)}$$

$$2\ NH_3 + 3\ O_3 \rightarrow N_2 + 3\ H_2O + 3\ O_2 \text{ (ammonia)}$$

$$C_2H_4 + 6\ O_3 \rightarrow 2\ CO_2 + 2\ H_2O + 6\ O_2 \text{ (ethylene)}$$

$$3\ H_2S + O_3 \rightarrow 3\ S + 3\ H_2O \text{ (hydrogen sulfide)}$$

Impregnated Media. Media used in the present invention may be impregnated with a chemical to enhance removal capacity. Such impregnation adds to the system's capability. A typical impregnate is potassium or sodium permanganate, a strong oxidizing agent.

$$20\ H_2S + 8\ KMnO_4 \rightarrow 3\ K_2SO_4 + K_2S + 8\ MnS + 8\ S + 20\ H_2O \text{ (hydrogen sulfide)}$$

$$3\ C_6H_5OH + 28\ KMnO_4 \rightarrow 28\ MnO_2 + 28\ KOH + 18\ CO_2 \text{ (phenol)}$$

Catalyst Conversion of Ozone and Radicals. A key element of the present invention is the ability to contain chemistry, ozone and radicals within the system where they can be scavenged and converted to harmless compounds in the presence of a catalyst. Typical reactions follow.

$$2\ O_3 \rightarrow 3\ O$$

$$2\ .OH \rightarrow H_2O + O^-$$

$$O^- + O^- \rightarrow O_2$$

$$O_3 + O^- \rightarrow 2\ O_2$$

$O_3 \rightarrow O_2 + O^-$ $O_3 + H_2O \rightarrow O_2 + 2 \cdot OH$

The design of the onsite chemistry air filtration system of the present invention incorporates mechanisms to control these chemistries if they are not consumed in the process.

The above chemicals and reactions are given as examples and are not a complete list of all possibilities. Cigarette smoke alone generates over 4,000 chemicals and compounds almost all of which are VOCs. Many everyday cleaning compounds, perfumes, off gases from plastics and furniture, and outside air borne contaminants can be found indoors. For normal environments, the above chemical capabilities will cover the contaminant load. If there are special contaminants, then a study of literature or laboratory testing must be done to determine final results.

While this invention has been described with particular reference to preferred embodiments thereof, it should be understood that variations and modifications could be made without departing from the spirit and scope of the invention as defined in the appended claims. The embodiments of the present invention described above are to be regarded in all respects as merely illustrative and not restrictive.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

In the present disclosure, the words "a" or "an" are to be taken to include both the singular and the plural. Conversely, any reference to plural items shall, where appropriate, include the singular.

All patents referred to herein, are hereby incorporated herein by reference, whether or not specifically done so within the text of this disclosure.

What is claimed is:

1. A method for filtering air, comprising the steps of:
providing an onsite chemistry air filtration system comprising a photochemical filtration section and a static gas phase filtration section, the static gas filtration section comprising a first media bed, the first media bed comprising at least one first media having a first useful life, and a second media bed, the second media bed comprised of at least one second media and configured to provide an indication of the first useful life of the at least one first media, wherein the static gas filtration section is disposed after the photochemical filtration section, and wherein the photochemical filtration section is configured to cleanse the at least one first media of the static gas filtration section; and
passing the air through the onsite chemistry air filtration system, wherein the air passes through the photochemical filtration section before the air passes through static gas filtration section.

2. The method for filtering air of claim 1 wherein the photochemical filtration section comprises at least one ultraviolet lamp and a photocatalytic material.

3. The method for filtering air of claim 2 wherein the at least one ultraviolet lamp generates light within a wavelength range of about 85 nm to about 300 nm.

4. The method for filtering air of claim 2 wherein the at least one ultraviolet lamp generates light at the wavelengths of about 185 nm and 254 nm.

5. The method for filtering air of claim 2 wherein the photocatalytic material is titanium dioxide.

6. The method for filtering air of claim 1 wherein the at least one first media comprises activated carbon.

7. The method for filtering air of claim 1 wherein the at least one second media comprises activated alumina impregnated with potassium permanganate.

8. The method for filtering air of claim 1 wherein the onsite chemistry air filtration system further comprises a conventional particulate filtration section, the conventional particulate filtration section comprising at least one particle filter, wherein the air passes through the conventional particulate filtration section before the air passes through the photochemical filtration section.

9. The method for filtering air of claim 1 wherein the onsite chemistry air filtration system further comprises a catalytic filtration section configured to convert ozone and scavenge radicals, wherein the air passes through the catalytic filtration section after the air passes through the photochemical filtration section.

10. The method for filtering air of claim 1 wherein the photochemical filtration section further comprises an electrostatically charged surface.

11. A method for filtering air using an onsite chemistry air filtration system, comprising the steps of:
passing the air through a photochemical filtration section;
passing the air through a static gas phase filtration section, the static gas filtration section comprising a first media bed, the first media bed comprising at least one first media having a first useful life, and a second media bed, the second media bed comprised of at least one second media and configured to provide an indication of the first useful life of the at least one first media, wherein the photochemical filtration section is configured to cleanse the at least one first media of the static gas filtration section.

12. The method for filtering air of claim 11 wherein the photochemical filtration section comprises at least one ultraviolet lamp and a photocatalytic material.

13. The method for filtering air of claim 12 wherein the at least one ultraviolet lamp generates light within a wavelength range of about 85 nm to about 300 nm.

14. The method for filtering air of claim 12 wherein the at least one ultraviolet lamp generates light at the wavelengths of about 185 nm and 254 nm.

15. The method for filtering air of claim 12 wherein the photocatalytic material is titanium dioxide.

16. The method for filtering air of claim 11 wherein the at least one first media comprises activated carbon.

17. The method for filtering air of claim 11 wherein the at least one second media comprises activated alumina impregnated with potassium permanganate.

18. The method for filtering air of claim 11 further comprising the step of passing the air through a conventional particulate filtration section, the conventional particulate filtration section comprising at least one particle filter, wherein the step of passing the air through the conventional particular filtration section occurs before the step of passing the air through the photochemical filtration section.

19. The method for filtering air of claim 11 further comprising the step of passing the air through a catalytic filtration section configured to convert ozone and scavenge radicals, wherein the step of passing the air through the catalytic filtration section occurs after the step of passing the air through the static gas filtration section.

20. A method for filtering air, comprising the steps of:
providing a fan to move the air;
moving the air through a conventional particulate filtration section, the conventional particulate filtration section comprising at least one particle filter;
moving the air through a photochemical filtration section, the photochemical filtration section comprising at least one ultraviolet lamp and a photocatalytic material, wherein the at least one ultraviolet lamp generates light at the wavelengths of about 185 nm and 254 nm, and wherein the photocatalytic material comprises titanium dioxide;
moving the air through a static gas phase filtration section, the static gas filtration section comprising a first media bed, the first media bed comprising at least one first media having a first useful life, and a second media bed, the second media bed comprised of at least one second media and configured to provide an indication of the first useful life of the at least one first media, wherein the photochemical filtration section is configured to cleanse the at least one first media of the static gas filtration section, wherein the at least one first media comprises activated carbon and the at least one second media comprises activated alumina impregnated with potassium permanganate;
moving the air through a catalytic filtration section configured to convert ozone and scavenge radicals.

* * * * *

UNITED STATES PATENT AND TRADEMARK OFFICE
CERTIFICATE OF CORRECTION

PATENT NO. : 7,828,940 B2
APPLICATION NO. : 12/635510
DATED : November 9, 2010
INVENTOR(S) : Jeffrey L. Roseberry et al.

Page 1 of 1

It is certified that error appears in the above-identified patent and that said Letters Patent is hereby corrected as shown below:

Column 14, Line 41: The term "$N_{2+3} + H_2O$" should be removed and replaced with the term "$N_2 + 3 H_2O$".

Column 14, Line 62: The reaction "$2 O_3 \rightarrow 3 O$" should be removed and replaced with the reaction "$2 O_3 \rightarrow 3 O_2$".

Signed and Sealed this
First Day of February, 2011

David J. Kappos
*Director of the United States Patent and Trademark Office*